United States Patent [19]

Staats et al.

[11] Patent Number: 4,603,590  
[45] Date of Patent: Aug. 5, 1986

[54] METHOD OF AND VESSEL FOR REMOVING SAMPLES FROM A BATH OF MOLTEN METAL

[75] Inventors: Gotthard Staats, Hemmersdorf; Horst Thome, Nalbach, both of Fed. Rep. of Germany

[73] Assignee: Aktien-Gesellschaft der Dillinger Hüttenwereke, Dillingen, Fed. Rep. of Germany

[21] Appl. No.: 738,776

[22] Filed: May 29, 1985

Related U.S. Application Data

[63] Continuation of Ser. No. 489,730, Apr. 29, 1983, abandoned.

[30] Foreign Application Priority Data

May 4, 1982 [DE] Fed. Rep. of Germany ....... 3216554

[51] Int. Cl.⁴ .............................................. G01N 1/12
[52] U.S. Cl. .............................. 73/864.58; 73/864.52; 73/DIG. 9
[58] Field of Search ........... 73/864.51, 864.52, 864.53, 73/864.58, DIG. 9

[56] References Cited

U.S. PATENT DOCUMENTS

| | | | |
|---|---|---|---|
| 3,332,288 | 7/1967 | Mladenovich | 73/864.52 |
| 3,559,452 | 2/1971 | Perbix et al. | 73/864.58 |
| 3,704,621 | 12/1972 | Zickfoose et al. | 73/864.58 |
| 3,774,453 | 11/1973 | Falk | 73/DIG. 9 |
| 3,967,505 | 7/1976 | Feichtinger | 73/864.52 |

OTHER PUBLICATIONS

Novosadov et al., "A Molten Wedge Specimen for Investigating the Reactions Between Iron and Molten Aluminium," Autom, Weld, vol. 23, No. 9, (Sep. 1970), pp. 4–7.

*Primary Examiner*—Stewart J. Levy
*Assistant Examiner*—John E. Chapman, Jr.
*Attorney, Agent, or Firm*—Peter K. Kontler

[57] ABSTRACT

A sample from a bath of killed molten steel which contains aluminum is removed with a vessel having a cover which undergoes at least partial disintegration on contact with molten metal and allows molten metal to fill the vessel as soon as the latter is lowered to a preselected level. The internal space of the vessel contains a strip of magnesium and a strip of zirconium. Magnesium evaporates with an explosion as soon as it is contacted by molten metal and thereby enters into a chemical reaction with oxygen in the vessel while also expelling the remaining air through the partially disintegrated cover to further reduce the likelihood of reaction between aluminum and air which is entrained with the immersed vessel. Zirconium dissolves in the metal which fills the vessel and bonds oxygen close to the surface surrounding the internal space of the vessel. The vessel has an inner envelope consisting of foundry sand and a suitable binder, a metallic outer envelope, and a liner which is surrounded by the inner envelope and includes a quartz tube as well as a bottom wall of sheet metal. When the molten metal hardens, the resulting billet is cut in half and the thus exposed surface is analyzed inwardly of the circumference to thus ensure that the test involves an examination of material which does not contain aluminum oxide whose development is caused by entrainment of some oxygen into the bath as a result of immersion of the vessel.

18 Claims, 3 Drawing Figures

METHOD OF AND VESSEL FOR REMOVING SAMPLES FROM A BATH OF MOLTEN METAL

This application is a continuation, of application Ser. No. 489,730, filed Apr. 29, 1983, and now abandoned.

BACKGROUND OF THE INVENTION

The present invention relates to a method of removing samples from a bath of killed molten metal, particularly for removing samples from a bath of molten steel for the purpose of ascertaining the aluminum content of steel. The invention also relates to improvements in a device which is utilized for the practice of the method.

It is already known to remove samples from a bath of molten metal by resorting to a vessel which has a destructible cover. The cover disintegrates on immersion of the vessel into the bath of molten metal as a result of heating on contact with molten metal and/or under the pressure of molten metal below the level of the upper surface of the bath. This allows molten metal to penetrate into the interior of the vessel. The withdrawn metal is allowed to set upon lifting of the vessel out of the bath, and the rigid metallic sample is then removed from the vessel for testing.

If a metallic alloy contains one or more ingredients (e.g., aluminum) which exhibit a high affinity to oxygen, it is necessary to subject the alloy to a careful analysis in order to ascertain the extent of the formation of scale which develops as a result of contact between air and the exposed surface of the bath as well as due to contact with air which is adjacent to the surfaces and/or has penetrated into the pores of the fireproof ladle. It has been found that the results of the analysis which is carried out upon samples obtained with resort to presently known methods and/or with resort to presently known sample removing instrumentalities are often highly misleading because the removed samples contain excessive amounts of oxidized ingredients which exhibit a pronounced affinity to oxygen. This is due to the fact that the vessel which is used for removal of samples is likely to entrap and/or otherwise carry along substantial quantities of oxygen in the air which has penetrated into the pores of the material of the vessel as well as air which contacts the exposed surface of the vessel prior to immerson into the bath. Some air is absorbed by the material along the exposed surfaces of the vessel, and additional air is held by the vessel as a result of chemisorption. Such air reacts with aluminum and/or with other readily oxidizable ingredients of the removed sample so that the condition of the sample does not accurately reflect the condition of the major part of the bath of molten metal in the ladle.

OBJECTS AND SUMMARY OF THE INVENTION

An object of the invention is to provide a novel and improved method of removing samples from a bath of molten metal, particularly steel, in such a way that the condition of the removed sample is more accurately indicative of the condition of the major part of the bath than that of samples which are obtained in accordance with heretofore known methods.

Another object of the invention is to provide a method which is carried out in such a way that the removal of samples does not involve contact of the material of the sample with appreciable quantities of oxygen.

A further object of the invention is to provide a method which is particularly suited for removal of samples from a bath of killed molten steel which contains aluminum and/or other readily oxidizable constituents.

An additional object of the invention is to provide a novel and improved implement for removal of samples from a bath of molten metal, especially for removal of samples from a bath of killed molten steel which contains aluminum and/or other ingredients exhibiting the same or similar affinity to oxygen.

Still another object of the invention is to provide a novel and improved vessel for removal of small quantities of molten metal from a bath which contains one or more readily oxidizable ingredients.

A further object of the invention is to provide a simple, inexpensive and dispensable vessel for removal of samples from a bath of molten steel.

Still another object of the invention is to provide a vessel which is constructed and assembled in such a way that it brings little or no air into contact with molten metal when it is immersed into the bath for the purpose of removing a sample therefrom.

Another object of the invention is to provide a vessel which can serve for removal of larger or smaller quantities of molten metal and which can be used with advantage as a superior substitute for heretofore known vessels.

One feature of the invention resides in the provision of a method of removing samples from a bath of killed molten metal with a vessel whose interior is sealed prior to contact with the bath, particularly for the purpose of determining the aluminum content of steel. The method comprises the steps of providing the vessel with a destructible wall (such wall can constitute the cover of an upright cylindrical vessel) which undergoes at least partial disintegration on contact with the molten metal of the bath, evacuating oxygen from the interior of the vessel, and immersing the vessel into the bath so that the destructible wall of the vessel undergoes at least partial disintegration and permits molten metal to penetrate into the interior of the immersed vessel.

The evacuating step can include reducing the pressure in the interior of the vessel below atmospheric pressure, i.e., establishing a more or less pronounced pressure differential between the interior and the exterior of the vessel. Alternatively, the evacuating step can include filling the interior of the vessel with an inert gas so that the gas expels air and hence oxygen from the interior of the vessel prior to the immersing step.

Still further, the evacuating step can comprise introducing into the interior of the vessel prior to the immersing step an effective amount of a substance (such as magnesium) having a high affinity to oxygen and a boiling point below the temperature of the bath of molten metal. Such substance can be introduced into the interior of the vessel in the form of a strip, band, web or the like (hereinafter called strip). The just mentioned step of introducing into the interior of the vessel an effective amount of magnesium or a like substance can be carried out in addition to the evacuating step, e.g., by introducing a strip of magnesium into the interior of the vessel prior to evacuation of oxygen. The strip of magnesium reacts with eventually present remnants of oxygen in the interior of the vessel as soon as it is contacted by the first spray, jet or stream of molten metal which penetrates into the interior of the vessel in response to at least partial disintegration of the wall.

The method can also comprise the step of introducing into the interior of the vessel prior to the immersing step an effective amount of a different second substance which is soluble in the bath and has a high affinity to oxygen and a boiling point above the temperature of the bath of molten metal. Such second substance can contain or consist of zirconium which is preferably introduced in the form of a strip.

Another feature of the invention resides in the provision of a vessel for removing samples from a bath of killed molten metal, particularly for the purpose of determining the aluminum content of steel. The vessel comprises an impermeable outer envelope and a porous inner envelope which consists of a heat-insulating material, which is surrounded by the outer envelope, and which defines a chamber for the sample. The vessel further comprises a destructible wall (preferably a cover) which is arranged to undergo at least partial disintegration on contact with molten metal and to thus permit penetration of molten metal into the chamber. The outer envelope can consist of sheet metal and the inner envelope preferably consists of or contains foundry sand and a binder for foundry sand. The vessel preferably further comprises a support for the envelopes, e.g., a yoke which is attached to the lower end of an immersion tube or bar and at least a portion of which is preferably embedded in the inner envelope.

The vessel can also comprise a liner which is disposed in the interior of the inner envelope and surrounds the chamber. The liner preferably consists of a material whose permeability is less than that of the inner envelope. For example, the liner can comprise a hollow cylindrical section consisting of silica glass and a bottom wall consisting of sheet metal. A layer of mineral glue can be interposed between the inner envelope and the liner.

The destructible wall preferably includes a portion whose resistance to disintegration on contact with molten metal of the bath is less pronounced than that of the remaining portion of the wall. This ensures that a jet of molten metal can penetrate into the chamber as soon as the destructible wall comes in contact with molten metal whereby the hot metal causes evaporation of the magnesium strip and/or melting of the zirconimum strip.

The novel features which are considered as characteristic of the invention are set forth in particular in the appended claims. The improved vessel itself, however, both as to its construction and the mode of utilizing the same, together with additional features and advantages thereof, will be best understood upon perusal of the following detailed description of certain specific embodiments with reference to the accompanying drawing.

DESCRIPTION OF THE PREFERRED EMBODIMENTS

Figure 1:
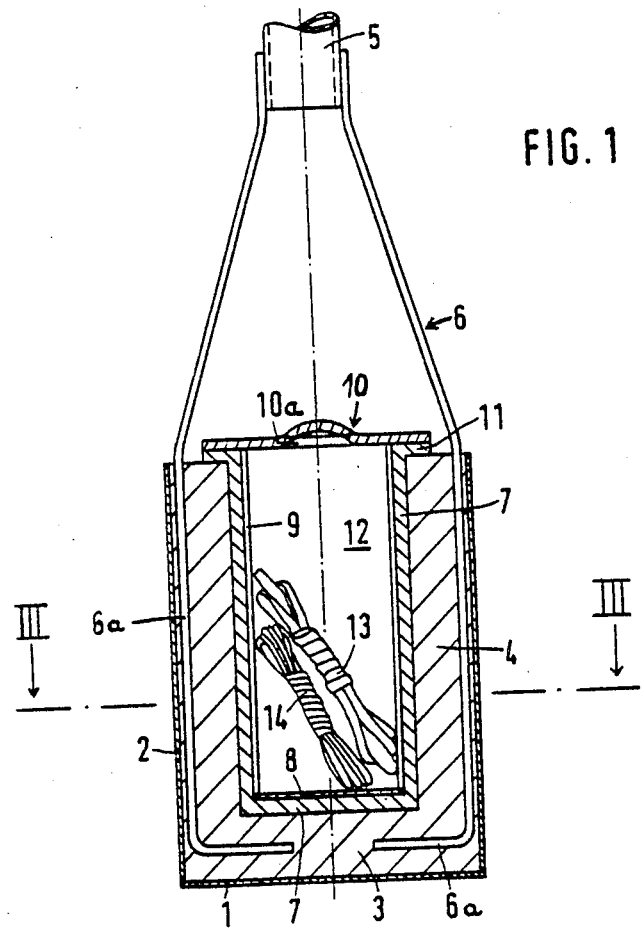
FIG. 1 is a somewhat schematic central vertical sectional view of a vessel which embodies one form of the invention.
Figure 2:
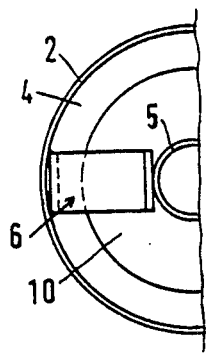
FIG. 2 is a fragmentary plan view of the vessel.
Figure 3:
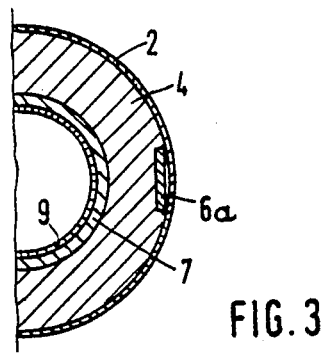
FIG. 3 is a fragmentary horizontal sectional view of the vessel substantially as seen in the direction of arrows from the line III—III of FIG. 1.

The vessel which is shown in FIG. 1 comprises an outer envelope including a bottom wall 1 and a cylindrical wall 2. Each of these walls is preferably made of sheet metal so that its permeability is low or nil. The vessel further comprises a relatively thick inner envelope including a bottom wall 3 inwardly adjacent to the much thinner bottom wall 1 of the outer envelope and a cylindrical wall 4 which is surrounded by the much thinner cylindrical wall 2 of the outer envelope. The material of the inner envelope is preferably molding or foundry sand whose particles are held together by a suitable binder of any known composition. A yoke-like support 6 has two downwardly extending L-shaped portions or legs 6a which are disposed diametrically opposite one another with reference to the common axis of the cylindrical walls 2, 4 and which are at least partially embedded in the material of the inner envelope. The exposed upper end portion of the support 6 is separably or permanently connected with a tubular pole 5 by means of which the vessel can be introduced into a bath of molten steel, not shown. The vertical portions of the legs 6a are closely adjacent to the external surface of the cylindrical wall 4 and their lower end portions are bent so that they are embedded in the material of the bottom wall 3.

The inner envelope including the walls 3 and 4 defines a cylindrical chamber 12 which is surrounded by a layer 7 of mineral glue for retention of a liner including a cylindrical section 9 surrounded by the wall 4 and a disc-shaped bottom section 8 overlying the bottom wall 3. The material of the cylindrical section 9 is silica glass (e.g., quartz) and the material of the bottom section 8 is sheet metal. The permeability of the liner including the sections 8 and 9 is much less pronounced than that of the porous inner envelope.

The vessel of FIG. 1 further comprises a destructible wall in the form of a circular cover 10 the marginal portion of which overlies and adheres to a ring-shaped flange 11 consisting of mineral glue and overlying a portion of the upper end face of the cylindrical wall 4. The cover 10 is destructible in response to heating and preferably consists of a metallic sheet material which undergoes at least partial disintegration under the action of heat and/or pressure when it is contacted by molten metal on immersion of the vessel into the bath. The layer 7 of mineral glue attracts the sections 8, 9 of the liner as well as the cover 10 during immersion of the vessel into the bath.

The chamber 12 contains a bundle of neatly looped magnesium strip 13 and a similar bundle of zirconium strip 14. For example, the magnesimum strip 13 can have a width of 3 mm and a thickness of 0.2 mm, and its weight is or approximates 2 grams if the volume of the chamber 12 is in the range of 200 ml. This is the presently preferred volume of the chamber. The quantity of zirconium which forms the bundle 14 is or can be selected in such a way that it is between five and six times the amount of aluminum in the sample which fills the chamber 12 when the vessel is immersed into a bath of molten aluminum-containing steel.

The part 5 may constitute a tube which is made of cardboard and is preferably manipulated by a machine in a manner well known from the art of immersion probes.

When the vessel is immersed into a bath of killed molten steel, the cover 10 disintegrates as a result of melting at the elevated temperature of the bath and/or in response to the pressure of molten material which acts thereagainst on immersion below the upper side of the bath. It is preferred to select the thickness of the cover 10 in such a way that it melts and permits molten material to penetrate into the chamber 12 when the vessel reaches a predetermined level below the upper surface of the bath. This can be readily determined by regulating the speed at which the vessel is lowered into the bath and by appropriate selection of the thickness and material of the cover 10. The first or foremost spurt of molten metal which penetrates into the chamber causes abrupt explosion-like evaporation of the magnesium strip 13 which results in a chemical reaction between the vapors and oxygen (if any) in the chamber 12. Any remaining oxygen (air) which does not react with evaporated magnesium is expelled from the chamber 12 by the vapors before the chamber 12 is filled with molten metal. In other words, contact between the magnesium strip 13 and the first stream or jet of inflowing molten metal can result in a chemical reaction between magnesium and oxygen and/or in complete expulsion of air from the chamber 12 prior to complete disintegration of the cover 10. The chamber 12 is filled with molten metal as soon as the expulsion of oxygen is completed, normally not later than on completion of melting of the material of the cover 10.

The filled vessel is maintained in the bath for a certain interval of time, e.g, for an interval of three seconds. The vessel is thereupon lifted by the support 6 and is held at a standstill above the bath for a period of between approximately 5 and 10 seconds to thus allow for at least partial setting and to thereby reduce the likelihood of splashing of the material which is confined in the chamber 12 during further manipulation of the filled vessel.

The hardened metal in the chamber 12 forms a billet a portion of which is thereupon made ready for testing by severing the vessel substantially midway between the upper and lower ends of the walls 2 and 4 (or perhaps slightly below such level). The material which is adjacent to the thus exposed surface of the billet and is disposed inwardly from the cylindrical section 9 of the liner is then subjected to an analysis in a manner not forming part of the invention.

Particles of aluminum oxide are likely to rise into the upper part of the chamber 12 during hardening of the material which fills the vessel upon extraction from the bath. Therefore, and if the billet is severed midway or approximately midway between the axial ends of the walls 2 and 4, that part of solidified metallic material which fills the lower part of the thus severed vessel is less likely to contain excessive quantities of aluminum oxide. Rising of aluminum oxide prior to setting of the material which fills the chamber 12 is promoted by the characteristics (heat-insulating property) of the material of the thick-walled inner envelope including the bottom wall 3 and the cylinder 4. Moreover, the volume of the chamber 12 is relatively large (as stated above, the presently preferred volume is or approximates 200 ml) which also contributes to relatively slow hardening of the material of the removed sample. It will be readily appreciated that the volume of the chamber 12 can be selected practically at will, i.e., the improved vessel can be used with equal advantage for removal of relatively large or relatively small quantities of molten metal.

As mentioned above, that portion of the billet which is to be analyzed is inwardly spaced from the cylindrical section 9 of the liner. This also contributes to prevention of the accumulation of excessive quantities of aluminum oxide in the tested portion of hardened metallic material. In other words, the just mentioned selection of the material which is to be analyzed ensures that any aluminum oxide which is formed as a result of penetration of oxygen from the internal surface and/or from the pores (if any) of the liner into the molten contents of the chamber 12 cannot influence the test. The likelihood of penetration of oxygen from the liner into molten metal is remote in view of the presence of the zirconium strip 14 which melts in regions adjacent to the inner side of the liner and attracts and binds oxygen which might have been brought into the bath by the section 8 and/or 9 of the liner.

The magnesium strip 13 can be replaced by other alkaline earth metals, by an alkali metal, by a metal hydride and/or zinc, i.e., by any one of a wide variety of substances which exhibit a pronounced affinity to oxygen.

The zirconium strip can be replaced by hafnium, titanium, silicon alloys, uranium, metals of the scandium group and/or the lanthanide series.

Moreover, effective amounts of magnesium (or an equivalent thereof) and/or zirconium (or an equivalent thereof) can be introduced into the chamber 12 in the form of shavings, fragments, powder or (especially in the case of zinc) in the form of a more or less coherent coat which is applied to the internal surface of the liner including the sections 8 and 9.

Still further, the material of the bottom wall 3 and/or cylindrical wall 4 of the inner envelope may be a fireproof lightweight concrete containing a suitable blowing agent. The cylindrical section 9 of the liner preferably consists of a silica glass; however, it can be replaced with a metallic tube without departing from the spirit of the invention. A metallic tube cannot always be readily separated from the billet.

It is also within the purview of the invention to provide the cover 10 with a weakened portion which disintegrates prior to the remaining portion of the cover on contact with molten metal in the bath. The dimensions of such weakened portion can be selected with a view to ensure the penetration of a relatively small quantity of molten metal into contact with the strips 13 and 14 before the major part of the chamber 12 is filled with molten metal. The configuration of the weakened portion can be such that its disintegration results in the penetration of a relatively thin stream or jet of molten metal into the interior of the chamber 12 a predetermined interval of time ahead of partial or complete destruction of the remaining (normally major) part of the cover 10. Since the speed at which the vessel is immersed into the bath is or can be regulated, the timing of disintegration of the weakened portion can be determined in advance with a very high degree of accuracy. The weakened portion is indicated at 10a; it will be noted that this weakened portion can be disposed at the center of the cover 10 and may constitute an upwardly bulging membrane whose thickness is less than the thickness of the remaining major portion of the cover 10. The weakened portion 10a can be formed by resorting to a simple tool which is caused to bear against the underside of the cover 10 so as to cause the central portion to bulge outwardly and which simultaneously reduces the thickness of such portion.

An important advantage of the improved method and vessel is that the vessel is much less likely to entrain substantial quantities of oxygen during immersion into the bath of killed molten metal. Heretofore, the quantity of oxygen entrained into the bath as a result of immersion of the vessel was disregarded due to failure to recognize that such oxygen can and actually does contribute to a distortion of the test which is carried out upon the samples of removed metallic material. A pronounced reduction of the quantity of oxygen which is entrained by the vessel during immersion into the bath is achieved due to the fact that the porosity of the outer envelope is low or nil and that the chamber 12 can be evacuated (i.e., the pressure therein reduced well below atmospheric pressure with attendant reduction of the amount of oxygen in the chamber) prior to application of the cover 10 which thereupon seals the chamber 12 from the surrounding atmosphere prior to and during immersion of the vessel into the bath. If desired, evacuation of oxygen from the chamber 12 prior to immersion of the vessel can be achieved by filling the chamber with an inert gas (e.g., a noble gas) whereby the inert gas expels air from the chamber before the latter is sealed by the cover 10.

Evacuation of oxygen from the chamber 12 is preferably achieved prior to immersion of the vessel. However, it is also possible to effect such evacuation while the vessel is in the process of penetrating into the bath. This can be achieved by insertion into the chamber 12 of an effective amount of magnesium or another substance exhibiting a pronounced affinity to oxygen and by selecting the rate of penetration of molten metal into the chamber 12 in such a way that the evaporation of magnesium entails a chemical reaction with oxygen in the chamber as well as expulsion of remaining oxygen from the chamber before the latter is filled with molten metal. The boiling point of magnesium is lower than the temperature of the bath of molten steel. Evaporation of magnesium in the chamber 12 in response to contact with the first spray of molten metal entails a minor explosion and such evaporation has been found to entail the development of a pronounced chemical reaction with oxygen and immediate expulsion of remaining traces of oxygen from the chamber before the latter is filled with molten metal. It has been found that such evaporation of magnesium can be resorted to in addition to evacuation of at least some oxygen prior to closing of the vessel by applying the cover 10 over the flange 11 of the intermediate layer 7 of mineral glue, or that the insertion of an effective amount of magnesium or an equivalent substance by itself suffices to effect timely evacuation or binding of oxygen in the chamber 12 before the latter is filled with molten metal. The first stream or jet of molten metal which causes evaporation of the magnesium strip 13 deposits and sets on the bottom section 8 of the liner and is thus remote from that portion of the sample which is actually tested if the sample is severed substantially midway between the bottom section 8 and the flange 11. Thus, the spray, jet or stream which has caused the evaporation of magnesium is not tested or analyzed at all because it sets before the bulk of molten metal penetrates into the chamber 12 subsequent to escape of vapors through that portion of the cover 10 which is first to disintegrate, e.g., through the aforementioned centrally located weakened portion 10a.

Insertion of the zirconium strip 14 (or of a substance exhibiting a similar affinity to oxygen, whose boiling point is above the temperature of molten metal in the bath and which can dissolve in molten metal) constitutes a desirable optional (safety) feature because zirconium intercepts any and practically all remaining traces of oxygen, i.e., that oxygen which is not expelled by and/or which does not react with magnesium. As explained above, zirconium binds oxygen which is absorbed by the liner, which is chemisorbed by the liner and/or which has undergone a chemical reaction with the liner. As also mentioned above, the quantity of zirconium in the chamber 12 is preferably many times the quantity of aluminum in the sample which ultimately fills the vessel.

The improved vessel is constructed and assembled with a view to ensure that the novel method can be practiced with maximum advantage. This is achieved in that the outer envelope exhibits a porosity which is a minute fraction of the porosity of the thick-walled heat-insulating inner envelope. Such envelopes ensure that the material in the chamber 12 sets gradually, i.e., hardening of the sample takes longer than in heretofore known bomb-shaped vessels, probes and the like. This enables the particles of aluminum oxide to rise in the material which fills the chamber 12 and to move away from the region which is analyzed subsequent setting of the sample. In the absence of such gradual setting of the sample in the vessel of the present invention, particles of aluminum oxide would be present in the analyzed region and would entail the making of a distorted test, i.e., the analysis (irrespective whether a spectral analysis, an X-ray fluorescence analysis or another analysis) would falsely indicate the presence of alloyed aluminum. The liner including the sections 8 and 9 seals the pores and the internal surface of the heat-insulating inner jacket from the chamber 12. If the vessel develops cracks (either during manufacture or as a result of thermal shock on immersion into the bath of molten metal), and the development of such cracks entails the penetration of some oxygen from the internal surface of from the pores of the inner envelope into the chamber 12, such oxygen is intercepted by zirconium close to the external surface of the body of metal, which ultimately fills the chamber and thereby preventing penetration of oxidized aluminum into the region which is analyzed subsequent to hardening of the sample.

It has been found that the aforedescribed vessel constitutes a substantial improvement over conventional vessels even if it does not contain magnesium and/or zirconium at the time of immersion into the bath. In other words, such vessel is capable of greatly reducing the quantity of oxygen which is entrained into the bath as a result of immersion of the vessel even if its chamber 12 is relieved of oxygen only and alone prior to the immersing step. The utilization of an inner envelope whose material and characteristics resemble those of a steel casting form is desirable and advantageous for a number of reasons. Such inner envelope exhibits highly satisfactory thermal insulating properties to ensure gradual setting of the body of metal in the chamber 12. Moreover, the inner envelope is simple and inexpensive, and it can be rapidly destroyed by resorting to a simple impacting tool in order to gain access to the billet in the chamber 12. Still further, the nature of the material of the inner envelope is such that the portions 6a of the support 6 can be readily embedded therein. The outer envelope including the walls 1 and 2 serves to reinforce the inner envelope and to reduce the likelihood of contact between oxygen in the pores of the walls 3, 4 and the material of the bath around the immersed vessel.

The liner including the sections 8 and 9 is simple and inexpensive. Moreover, the section 9 does not exhibit a tendency to adhere to the billet in the chamber 12. The provision of a layer of mineral glue allows for simple and inexpensive but reliable retention of the sections 8, 9 and cover 10 in optimum positions.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of removing a sample from a killed steel bath having a readily oxidizable constituent, particularly for the purpose of determining the aluminum content of the steel, comprising the steps of immersing a sampling vessel in said bath, said vessel defining a chamber which accommodates an effective amount of a substance having a high affinity for oxygen and a boiling point below the temperature of said bath, and said vessel being provided with a cover having a first portion and a second portion and closing said chamber; eliminating substantially all reactive oxygen from said chamber by destroying said first portion of said cover, introducing an initial part of said sample into said chamber through the opening created by destruction of said first portion, and vaporizing at least part of said substance with said initial part to thereby bind reactive oxygen and/or expel reactive oxygen from said chamber; and admitting the main part of said sample into said chamber subsequent to the eliminating step, the admitting step including destroying said second portion of said cover.

2. The method of claim 1, wherein said eliminating step includes reducing the pressure in the interior of the chamber below atmospheric pressure prior to introducing said initial part of said sample into said chamber.

3. The method of claim 1, wherein said eliminating step includes filling the interior of the chamber with an inert gas prior to introducing said initial part of said sample into said chamber.

4. The method of claim 1, wherein said substance is introduced into the interior of the chamber in the form of a strip.

5. The method of claim 1, wherein the eliminating step comprises introducing into the interior of the chamber prior to introduction of said initial part of said sample an effective amount of another substance which is soluble in the bath and has a high affinity to oxygen and a boiling point higher than the temperature of the bath.

6. The method of claim 5, wherein said other substance contains zirconium.

7. The method of claim 5, wherein said other substance is introduced into the interior of the chamber in the form of a strip.

8. The method of claim 1, wherein said eliminating step includes eliminating reactive oxygen on internal surfaces and in pores of said vessel which communicate with said chamber.

9. The method of claim 1, wherein said substance is magnesium.

10. The method of claim 9, wherein said constituent is aluminum.

11. A vessel for removing samples from a bath of molten metal, particularly for the purpose of determining the aluminum content of killed steel, comprising an insulating envelope containing foundry sand; and a substantially impermeable liner in the interior of said insulating envelope and defining a chamber for a sample, said liner including a hollow cylindrical section consisting of silica glass, and a bottom wall consisting of sheet metal.

12. A vessel for removing samples from a bath of molten metal, particularly for the purpose of determining the aluminum content of killed steel, comprising an insulating envelope containing foundry sand; a substantially impermeable liner in the interior of said insulating envelope and defining a chamber for a sample; and a layer of mineral glue between said liner and said insulating envelope.

13. The vessel of claim 12, comprising a destructible wall which seals said chamber and is designed to undergo at least partial disintegration upon contact with the bath.

14. A vessel for removing samples from a bath of molten metal, particularly for the purpose of determining the aluminum content of killed steel, comprising an insulating envelope containing foundry sand; a substantially impermeable liner in the interior of said insulating envelope and defining a chamber for a sample; and a destructible wall which seals said chamber and is designed to undergo at least partial disintegration upon contact with the bath, said destructible wall including a cover, and said cover including a portion whose resistance to disintegration on contact with molten metal of the bath is greater than that of the remaining portion of said cover.

15. The vessel of claim 14, wherein said insulating envelope contains a binder for said foundry sand.

16. The vessel of claim 14, further comprising a support including a portion which is at least partially embedded in the insulating envelope.

17. The vessel of claim 14, wherein said liner includes a hollow cylindrical section and a bottom wall.

18. The vessel of claim 14, comprising an outer envelope which surrounds said insulating envelope and consists at least in part of sheet metal.

* * * * *